(12) United States Patent
Tan et al.

(10) Patent No.: US 8,580,958 B1
(45) Date of Patent: *Nov. 12, 2013

(54) TWO-PHOTON ABSORBING POLYHYDROXY DIPHENYLAMINO-DIALKYLFLUORENE-1,3,5-TRIAZINE MOLECULES

(75) Inventors: Loon-Seng Tan, Centerville, OH (US); Ramamurthi Kannan, Cincinnati, OH (US); Matthew Dalton, Bellbrook, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 126 days.

This patent is subject to a terminal disclaimer.

(21) Appl. No.: 13/239,606

(22) Filed: Sep. 22, 2011

(51) Int. Cl.
  *C07D 251/24* (2006.01)
  *H05B 33/14* (2006.01)

(52) U.S. Cl.
  USPC .............................. 544/180; 514/241; 257/40

(58) Field of Classification Search
  USPC ........................................... 544/180; 514/241
  See application file for complete search history.

(56) References Cited

U.S. PATENT DOCUMENTS

| | | | |
|---|---|---|---|
| 6,300,502 B1 | 10/2001 | Kannan et al. | |
| 6,538,098 B1 | 3/2003 | Goldfinger | |
| 6,555,682 B1 | 4/2003 | Kannan et al. | |
| 6,680,016 B2 | 1/2004 | Wang et al. | |
| 6,730,793 B1 | 5/2004 | Kannan et al. | |
| 6,867,304 B1 | 3/2005 | Tan et al. | |
| 7,026,432 B2 | 4/2006 | Charati et al. | |
| 7,067,674 B1 | 6/2006 | Kannan et al. | |
| 7,319,151 B1 | 1/2008 | Tan et al. | |
| 7,960,471 B1 | 6/2011 | Tan et al. | |
| 8,173,763 B1 | 5/2012 | Tan et al. | |
| 8,318,888 B1 * | 11/2012 | Tan et al. | 528/73 |

OTHER PUBLICATIONS

Dalton, Matthew J.; Kannan, Ramamurthi; Haley, Joy E.; He, Guang-S.; McLean, Daniel G.; Cooper, Thomas M.; Prasad, Paras N.; Tan, Loon-Seng, "Aromatic Polyimides Containing Main-Chain Diphenylaminofluorene-Benzothiazole Motif: Fluorescence Quenching, Two-Photon Properties, and Exciplex Formation in a Solid State" Macromolecules 2011, 44(18), 7194-7206.
Jhaveri, Shalin J.; McMullen, Jesse D.; Sijbesma, Rint; Tan, Loon-Seng; Zipfel, Warren; Ober, Christopher K. Direct Three-Dimensional Microfabrication of Hydrogels via Two—Photon Lithography in Aqueous Solution. Chemistry of Materials (2009), 21(10), 2003-2006.
Rogers, Joy E.; Slagle, Jonathan E.; McLean, Daniel G.; Sutherland, Richard L.; Brant, Mark C.; Heinrichs, James; Jakubiak, Rachel; Kannan, Ramamurthi; Tan, Loon-Seng; Fleitz, Paul A. Insight into the Nonlinear Absorbance of Two Related Series of Two—Photon Absorbing Chromophores. Journal of Physical Chemistry A (2007), 111(10), 1899-1906.
He, Guang S.; Tan, Loon-Seng; Zheng, Qingdong; Prasad, Paras N. Multiphoton Absorbing Materials: Molecular Designs, Characterizations, and Applications. Chemical Reviews (Washington, DC, United States) (2008), 108(4), 1245-1330.
Kannan, Ramamurthi; He, Guang S.; Lin, Tzu-Chau; Prasad, Paras N.; Vaia, Richard A.; Tan, Loon-Seng. Toward Highly Active Two-Photon Absorbing Liquids. Synthesis and Characterization of 1,3,5-Triazine-Based Octupolar Molecules. Chemistry of Materials (2004), 16(1), 185-194.

(Continued)

*Primary Examiner* — Venkataraman Balasubramanian
(74) *Attorney, Agent, or Firm* — AFMCLO/JAZ; Chastity Whitaker

(57) ABSTRACT

Provided are novel 2PA-active monomers of the formula:

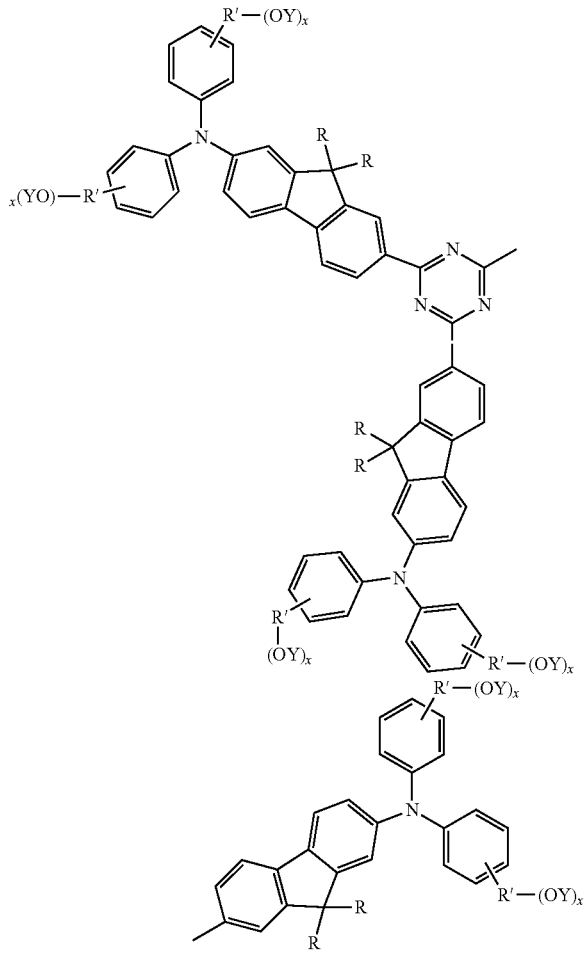

wherein Y=H, acrylic or methacrylic moiety; R is a linear or branched alkyl group, —$C_mH_{2m+1}$, where m=1-6 or an alkylether group, —$(CH_2CH_2O)_p$Me, where p=1-5. The number of R'—(OH)$_x$ groups, attached to the phenyl rings of the triarylamine moiety either in a para or a meta position, could be 3 or 6 per molecule, or mixtures of molecules containing 3, 4, 5, 6 in various ratios and wherein x=1, 2, or 3. R' is a linear or branched alkyl group such as —$C_mH_{2m}$, where m=1-6, i.e. linear —$(CH_2)_m$, where m=2-6, or branched alkyl group such as —$CH_2CH(R'')$—, where R''=—$(CH_2)_lCH_3$, where l=2-6.

2 Claims, No Drawings

(56) References Cited

OTHER PUBLICATIONS

He, Guang S.; Lin, Tzu-Chau; Dai, Jianming; Prasad, Paras N.; Kannan, Ramamurthi; Dombroskie, Ann G.; Vaia, Richard A.; Tan, Loon-Seng. Degenerate two-photon-absorption spectral studies of highly two-photon active organic chromophores. Journal of Chemical Physics (2004), 120(11), 5275-5284.

Kannan, Ramamurthi;He, Guang S.; Yuan, Lixian; Xu, Faming; Prasad,Paras N.; Dombroskie, Ann G.;Reinhardt, Bruce A.;Baur, Jeffery W.; Vaia, Richard A.; Tan, Loon-Seng. Diphenylaminofluorene-Based Two-Photon-Absorbing Chromophores with Various-Electron Acceptors. Chemistry of Materials (2001), 13 (5), 1896-1904.

Ambrosio, A.; Orabona, E.; Maddalena, P.; Camposeo, A.; Polo, M.; Neves, A. A. R.; Pisignano, D.; Carella, A.; Borbone, F.; Roviello, A., Two-photon patterning of a polymer containing Y-shaped azochromophores. Applied Physics Letters (2009), 94(1), 011115/1-011115/3.

Dong-Seon Won, Jin-Hyang Kim, Hyo Jin No, You Jin Cho, Ju-Yeon Lee, Bum Ku Rhee, Hee-Dok Choi "Synthesis and nonlinear optical properties of a novel polyurethane containing cyanovinylthiophene with enhanced thermal stability of dipole alignment for electro-optic applications," Polymer International (2010), 59(2), pp. 162-168.

Beecher, J. E.; Frechet, J. M.; Willand, C. S.; Robello, D. R.; Williams, D. J. "Concurrent stabilization and imaging of a novel polymer for second harmonic generation via in situ photopolymerization" From Report (1994), (TR-14-ONR; Order No. AD-A278 912), 70 pp.. Language: English, Database: CAPLUS.

Yuxia, Z.; Zhao, L.; Ling, Q.; Jianfen, Z.; Jiayun, Z.; Yuquan, S.; Gang, X.; Peixian, Y. "Synthesis and characterization of a novel nonlinear optical polyurethane polymer ," European Polymer Journal (2001), 37(3), 445-449.

J. R. Smith et al., "Space durable polymer/carbon nanotube films for electrostatic charge mitigation," Polym., vol. 45 (2004) 825-836.

H. Kong et al., "Controlled functionalization of multiwalled carbon nanotubes by in situ atom transfer radical polymerization," JACS., vol. 126 (2004) 412-413.

J-B Baek et al., "Improved syntheses of poly(oxy-1,3-phenylenecarbonyl-1,4-phenylene) and related poly(ether-ketones) using polyphosphoric acid/P2O5 as polymerization medium," Polym., vol. 44 (2003) 4135-4147.

J. L. Bahr et al., "Covalent chemistry of single-wall carbon nanotubes," J. Mater. Chem., vol. 12 (2002) 1952-1958.

K. A. Watson et al., "Polyimide/carbon nanotube composite films for potential space applications," SAMPE Technical Conf., vol. 33 (2001) 1551-1560.

B. Maruyama et al., "Carbon nanotbes and nanofibers in composite materials," SAMPE J., vol. 38 (2002) 11 pages total.

M.S.P. Shaffer, "Polystyrene grafted multi-walled carbon nanotubes," Chem. Comm. (2002) 2074-2075.

C. Park et al., "Dispersion of single wall carbon nanotubes by in situ polymerization under sonication," Chem. Phys. Lett, vol. 364 (2002) 303-308.

N. Tagmatarchis et al., "Sidewall functionalization of single-walled carbon nanotubes through electrophilic addition," Chem. Comm. (2002) 2010-2011.

Y. Iwakura et al., "Syntheses of aromatic polyketones and aromatic polyamide" J. Polym. Sci., vol. 6 (1968) 3345-3355.

United States Patent and Trademark Office, Non-Final Office Action in U.S. Appl. No. 10/963,469, mailed Sep. 26, 2007, 7 pages total.

United States Patent and Trademark Office, Final Office Action in U.S. Appl. No. 10/963,469, mailed Apr. 8, 2008, 9 pages total.

United States Patent and Trademark Office, Advisory Action in U.S. Appl. No. 10/963,469, mailed Jul. 2, 2008, 6 pages total.

* cited by examiner

TWO-PHOTON ABSORBING POLYHYDROXY DIPHENYLAMINO-DIALKYLFLUORENE-1,3,5-TRIAZINE MOLECULES

RIGHTS OF THE GOVERNMENT

The invention described herein may be manufactured and used by or for the Government of the United States for all governmental purposes without the payment of any royalty.

SUMMARY OF THE INVENTION

The present invention relates to cross-linked or network polymers containing covalently bound chromophores with large, effective two-photon absorption cross-sections in near-infra-red spectral region and good linear transmission in the visible region.

BACKGROUND OF THE INVENTION

Two-photon or multiphoton absorption occurs through the simultaneous absorption of two or more photons via virtual states in an absorbing medium, with the former being more common. For a given chromophore, these absorption processes take place at wavelengths much longer than the cut-off wavelength of its linear (single-photon) absorption. In the case of two-photon absorption (2PA), two quanta of photons may be absorbed from a single light source (degenerate 2PA) or two sources of different wavelengths (non-degenerate 2PA). While multiphoton absorption processes have been theoretically described in 1931 and experimentally confirmed about 30 years later, this field remained dormant largely due to the lack of materials with sufficiently large two-photon sensitivity, quantified as two-photon cross-section ($\sigma_2'$), which is usually expressed in the units of Göppert-Mayer (1 GM=$1^{-50}$ cm$^4 \cdot$s$\cdot$photon$^{-1}\cdot$molecule$^{-1}$).

Then, in the mid-1990s, several new classes of chromophores exhibiting very large effective $\sigma_2'$ values were reported. In conjunction with the increased availability of ultrafast high-intensity lasers, the renewed interest has not only sparked a flurry of activities in the preparation of novel dye molecules with enhanced $\sigma_2'$ values, but also in advancing many previously conceived applications based on 2PA process in photonics and biophotonics, which are now enabled by these new chromophores. It is important to recognize the following useful features of the 2PA phenomenon based on the fact that 2PA scales nonlinearly with the squared intensity of the incident laser beam: (a) upconverted emission, whereby an incident light at lower frequency (energy) can be converted to an output light at higher frequency, for instance, near infrared (NIR) to ultraviolet (UV) upconversion; (b) deeper penetration of incident NIR light (into tissue samples, for example) than UV light, which may be hazardous with prolonged exposure; (c) highly localized excitation, as compared with one-photon processes, allowing for precise spatial control of in situ photochemical or photophysical events in the absorbing medium, thereby minimizing undesirable activities, such as, photodegradation or photobleaching; and (d) fluorescence, when properly manipulated, that would allow for information/signal feedback or amplification in conjunction with other possible, built-in effects, such as, surface plasmonic enhancement.

It is anticipated that further ingenious utilization of these basic characteristics will lead to practical applications other than the ones that have already emerged in such diverse areas as bio-medical fluorescence imaging, data storage, protection against laser damage, microfabrication of microelectromechanical systems (MEMS), photodynamic therapy, etc. In the past decade or so, significant advances have been made in the fundamental understanding of general structure-property relationship that has led to the design and synthesis of two-photon absorbers with very large cross-section values. Although further enhancement of 2PA cross-section is still possible, as suggested by a number of theoretical studies, for certain applications the two-photon-property requirement has essentially been met by the state-of-art chromophores. Because of the possible property-processing/fabrication trade-off, the secondary properties, e.g., thermal and mechanical properties, which are important to material processing into various useful forms (films, coatings, fibers, windows, etc.) and configurations, should be addressed. For the aforementioned solid forms, polymers can offer many advantages, such as the flexibility in fine-tuning the material properties and the availability of many processing options.

Accordingly, it is an object of the present invention to provide two-photon absorbing (2PA) chromophores with molecular features that are amenable to hyper-branching polymerization or network-forming polymerization with suitable co-monomers containing reactive functions, such as organic isocyanate, carboxylic acids, acid chlorides, anhydride-acid chloride, anhydride-carboxylic acid, as well as silicon-based co-monomers, such as tetra-alkoxy silane Si(OR)$_4$, commonly used in sol-gel processing of organically modified silicate glasses. The 2PA chromophores could also be further converted to thermosettable resins, including, but not limited to, acrylate and vinyldimethylsiloxane resins via reaction of alcohol groups with acrylic acid chloride or reaction of alcohol with vinyldimethylsilyl chloride, respectively. These thermosettable resins could be obtained with or without co-monomers via conventional free-radical polymerization or catalytic hydrosilylation processes.

Specifically, the main objective is to provide new compositions of matter for 2PA-active chromophores with a structural motif in which a 1,3,5-triazine core is triply connected to tertiary amino endgroups via 9,9-dialkyfluorenyl bridges. Another objective is to provide the methods for the preparation of these compounds, the compositions, and useful derivatives, which are obvious to those skilled in the art of thermosetting polymers.

Other objects and advantages of the invention will be set forth, in part, in the description which follows and, in part, will be obvious from the description, or may be learned by practice of the invention. The objects and advantages of the invention may be realized and attained by means of the instrumentalities and combinations particularly pointed out in the appended claims.

SUMMARY OF THE INVENTION

In accordance with the present invention, 2PA-active polyol monomers and acrylate/methacrylate derivatives thereof having the formula:

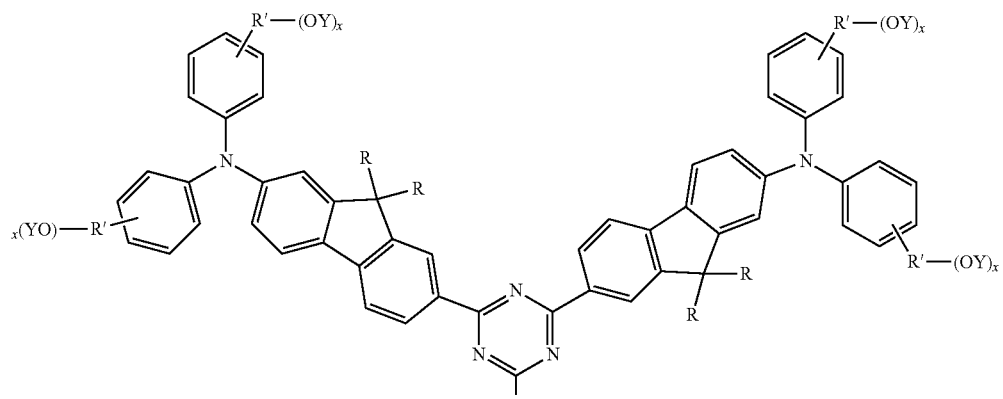

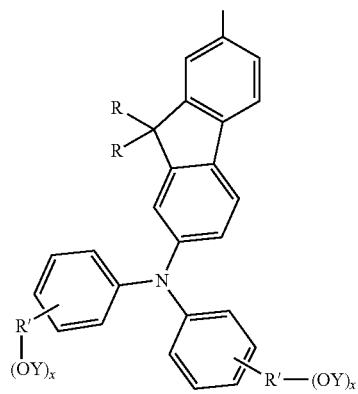

wherein Y is hydrogen, a thermally self-polymerizable acrylic or a methacrylic group; R is an alkyl group of the formula —$C_mH_{2m+1}$, where m=1-6 or an alkylether group of the formula —$(CH_2CH_2O)_p$Me, where p=1-5. The R'—$(OY)_x$ groups are attached to the phenyl rings of the triarylamine moiety in a para position or a meta position, wherein x=1, 2, or 3 such that there can be 3 or 6 per molecule, or mixtures of molecules containing 3, 4, 5, 6 in various ratios. R' is an alkyl group, such as —$C_mH_{2m}$, where m=1-6 (e.g., linear —$(CH_2)_m$, where m=2-6, or branched alkyl group such as —$CH_2CH(R'')$— and R''=—$(CH_2)_lCH_3$, where I=2-6).

DETAILED DESCRIPTION OF INVENTION

A generic structure of the parent polyhydroxy 1,3,5-triazine-based AFX chromophores (generically identified as AF-452-TOH; a specific example is AF-452-6OH, i.e., T=6) is shown below:

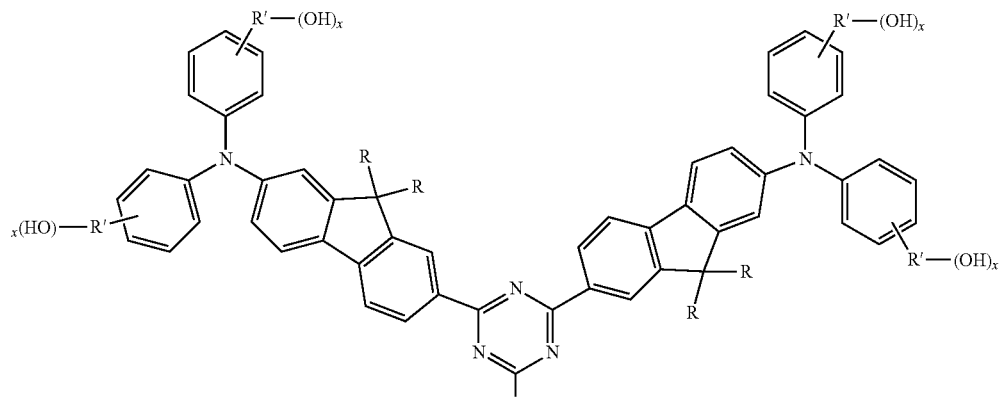

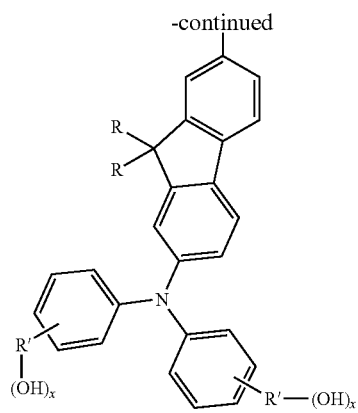

wherein R is an alkyl group of the formula —$C_mH_{2m+1}$, where m=1-6 or an alkylether group of the formula —$(CH_2CH_2O)_p$Me, where p=1-5. The R'—$(OH)_x$ groups, wherein x=1, 2, or 3, are attached to the phenyl rings of the triarylamine moiety either in a para position or a meta position, and can be 3 or 6 per molecule, or mixtures of molecules containing 3, 4, 5, 6 in various ratios. R' is an alkyl group, such as —$C_mH_{2m}$, where m=1-6 (e.g., linear —$(CH_2)_m$, where m=2-6, or branched alkyl group —$CH_2CH(R'')$—, where R''=—$(CH_2)_lCH_3$, where l=2-6).

As an illustration, a hexahydroxy 1,3,5-triazine-based AF-450 derivative, designated as AF-452-60H was synthesized following the synthetic scheme shown in Scheme 1 and briefly described in the following paragraph.

The convergent synthesis of AF-452-60H (compound 9 in Scheme 1) was accomplished in two parallel sequences followed by a converging sequence: (i) a 4-step sequence to a protected 3-O-alkylated diphenylamine intermediate 3, (ii) a 3-step sequence to the tris-7-(bromofluorene)triazine intermediate 7 and (ii) a 2-step sequence to AF-452-60H 8. Briefly, the first sequence was started with tris-1,1,1-(hydroxymethyl)ethane, which was first protected as an acetonide derivative, i.e., 2,2,5-trimethyl-5-hydroxymethyl-1,3-dioxane (compound 1) in either reaction (i) or reaction (ii), as indicated in Scheme 1. A Mitsunobu reaction of compound 1 with 3-bromophenol furnished the corresponding bromophenoxy-methyltrimethyl-1,3-dioxane 2 in 85% yield [Scheme 1, reaction (iii)]. The same compound 2 could also be obtained in 59% yield from a copper-catalyzed reaction between 3-bromoiodobenzene and compound 1 [Scheme 1, reaction (iv)]. Compound 2 was aminated with aniline to produce the diphenylamine intermediate 3 [Scheme 1, reaction (v)]. In the second sequence, 2,7-dibromo-9,9-diethylfluorene 4 was first monoformylated to form 7-bromodiethylfluorene-2-aldehyde 5, which was then converted to the nitrile intermediate 6 in 93% yield [Scheme 1, reactions (vi) and (viii), respectively]. A less satisfactory conversion of the aldehyde intermediate 5 to the nitrile intermediate 6 via a hydroxyl-imine intermediate was also conducted [49% yield, Scheme 1, reaction (vii)]. The nitrile intermediate 6 was subsequently and catalytically trimerized in trifluoromethanesulfonic acid to afford the tribromo-1,3,5-triazine intermediate 7 in 95% yield [Scheme 1, reaction (ix)]. Covalently joining the triazine component 7 with the diphenylamine component 3 with the assistance of a Pd-catalyzed amination gave the precursor chromophore protected as an acetonide 8, [Scheme 1, reaction (x)]. Removal of the acetone protecting groups from 8 was accomplished by mixing and stirring 8 together with Dowex-50Wx2 (acid-form) resin, and the desired product, AF-452-60H 9, was obtained in 90% yield [Scheme 1, reaction (xi)].

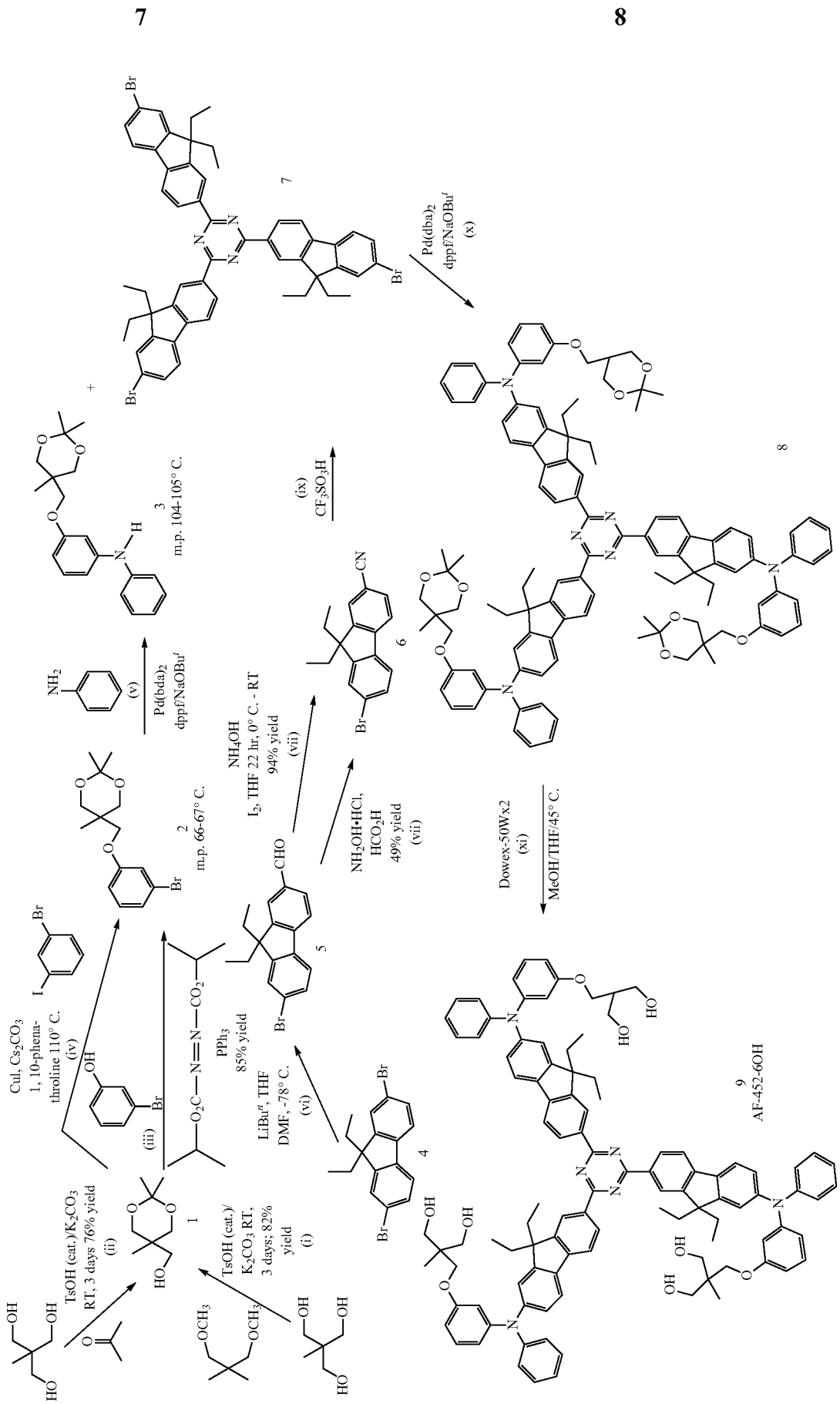

The hexahydroxyl compound 9 (in Scheme 1), which contains three sets of 1,3-diols, is expected to react with a wide range of industrially useful electrophiles, such as the ones that contain carbonyl (i.e., ketone, aldehyde, carboxylic acid, acid chloride, and anhydride isocyanate), and halosilyl groups. Thus, polymerizable derivatives including but not limited to acrylate/methacrylate resins could be generated from compound 9 with appropriately functionalized reagents.

Two-Photon Properties:

The linear optical and two photon properties for the newly synthesized dyes are expected to be similar to those of related AFX chromophores, namely AF-450, AF-455 and AF-457, which are described in U.S. Pat. No. 6,555,682. The effective 2PA cross-sections ($\sigma_2'$, 1 GM=$10^{-50}$ cm$^4$-sec/photon-molecule; 15% uncertainty) of these AFX chrmophores were measured by a nonlinear transmission (NLT) technique in THF solution (0.02 M) at 800 nm with ~8 ns laser pulses and found to be in the range of 28,000-40,000 GM. The two-photon spectra of these AFX chromophores have also been determined by a femtosecond, degenerate white-light continuum technique in THF, ranging from 600 nm to 900 nm with the peak values for the intrinsic 2PA cross-section found in the range of 200 GM to 220 GM at 779 nm.

The chromophoric monomers of this invention can be synthesized following the procedures given in the following Examples, which illustrate the invention:

EXAMPLE 1

2,7-Dibromofluorene

To a mechanically stirred mixture of fluorene (113.76 g., 0.68 mol), iodine (1.96 g, 0.0077 mol), and methylene chloride (750 mL), bromine (74 mL, 1.44 mol) diluted with methylene chloride (100 mL) was added dropwise at room temperature over a period of 1.5 hours. After 5 min, a solution of sodium bisulfite (15.0 g) in water (100 mL) was added and the mixture was stirred for 30 min, when the mixture became colorless. Water (750 mL) was then added, and methylene chloride was distilled off. The product slurry was filtered, and the product was air-dried, 220.5 g, m.p. 151° C. (sh), 156-160° C. This material was used in the next step without further purification.

EXAMPLE 2

2,7-Dibromo-9,9-diethylfluorene

To a mechanically stirred mixture of 2,7-dibromofluorene (66.5 g, 0.205 mol) (commercially-available), powdered potassium hydroxide (56.0 g, 1.0 mol), potassium iodide (3.4 g) and DMSO (150 mL), cooled to 1 ooc, ethyl bromide (40 mL, 58.4 g, 0.536 mol) was added dropwise over 45 min. The mixture turned from red to light purple. After allowing the temperature to warm to 20° C., the mixture was left overnight to stir and poured into water, 77.0 g (98.7% yield), m.p. 144-153° C. The product was then recrystallized from hexane (550 mL) with charcoal treatment, and collected in two crops, m.p. 154-157° C. and 153-154° C., totaling 60.36 g (77.4% yield).

EXAMPLE 3

7-Bromo-9,9-diethyl-fluorene-2-carboxaldehyde

To a mechanically stirred solution of 9,9-diethyl-2,7-dibromofluorene (59.38 g, 0.1563 mol), in THF (325 mL), cooled in dry ice-ethanol bath, n-butyllithium (104 mL of 1.6 M solution in hexanes, 0.1664 mol, 1.06 eq) was added dropwise over 25 min. After 20 min, DMF (17 mL, 0.22 mol) in THF (30 mL) was added, and the mixture was stirred in the cooling bath for 1.5 hr, and outside the bath for 1 hr. The reaction was then cooled to 5° C., and treated with hydrochloric acid (12.5 of concentrated hydrochloric acid diluted with 50 mL water). The mixture was diluted with 200 mL of toluene, and the aqueous phase was separated and extracted with 200 mL of toluene. The combined organic phase was washed with dilute sodium bicarbonate solution, dried over magnesium sulfate, and concentrated. The residual solids were recrystallized from heptane-ethyl acetate (9:1), to get colorless solids, 40.29 g (78.4% yield) m.p. 126-128° C. The mother liquor after chromatography over 150 g silica gel, elution with 1:1 heptane-toluene, and trituration of residual solids in hexanes gave additional product, 6.56 g (12.8% yield, total 91% yield), m.p. 126-128° C. Mass Spec: m/z 328, 330, (M$^+$). A sample for analysis was prepared by recrystallization from hexanes, m.p. 127-129° C. Analysis: Calculated for $C_{18}H_{17}BrO$, C, 65.55, H, 5.20, and Br, 24.27%. Found, C, 65.60, H, 5.51, and Br 24.71%.

EXAMPLE 4

7-Bromo-9,9-diethyl-fluorene-2-carboxaldehyde

To a mechanically stirred mixture of 7-bromofluorene-9, 9-diethyl-2-carboxaldehyde (32.0 g, 97.2 mmol), THF (400 mL), 28% ammonium hydroxide solution (800 mL), cooled to 5° C., iodine (16.0 g, 60.0 mmol) was added in portions, and the mixture was allowed to warm to room temperature. After 5 hours, the mixture was cooled and a second portion of iodine (16.0 g, 60.0 mmol) was added, and the stifling was continued for 18 hr. Toluene (600 mL) was added, and the organic phase was washed with water, dried, and concentrated. The residue was dissolved in hot hexanes (75 mL), and cooled. The crystalline nitrile product that separated upon cooling was collected, 29.88 g (94% yield), m.p. 87-89° C. Mass spec: m/z 325, 327 (M+).

An alternative but less satisfactory synthesis was conducted as follows: A mixture of 7-bromo-9,9-diethylfluorene-2-carboxaldehyde (3.29 g, 10.0 mmol), hydroxylamine hydrochloride (0.9 g, 10.0 mmol), and formic acid (15 mL), was held at reflux for 2 hours, cooled and filtered. The filtrate was worked up by extraction into toluene, washing the extract with water, and bicarbonate solution, drying and concentration. The residue was combined with the formic acid-insoluble solids and chromatographed over silica gel. There were obtained, the desired aldehyde product, 1.58 g (49%), m.p. 85-87° C., mass spectrum (m/z): 325, 327 (M$^+$); the amide by-product, 0.42 g (12%), m.p. 179-184° C., mass spectrum (m/z): 343, 345 (M$^+$); and the oxime by-product, m.p. 104-107° C., 0.17 g (5%), mass spectrum (m/z): 343 (M$^+$)

EXAMPLE 5

2,2,5-Trimethyl-5-hydroxymethyl-1,3-dioxane

To a solution of 1,1,1-tris(hydroxymethyl)ethane (50.4 g) in acetone (dried over calcium chloride, 550 mL), 4-toluenesulfonic acid monohydrate (0.4 g) was added and stirred at room temperature for 3 days. Potassium carbonate (2.0 g) was added, and the mixture was filtered and concentrated. The residue was taken in dichloromethane (200 mL), and the solution was washed with water (2×75 mL), dried, and concentrated. The residual liquid, 54.75 g, was distilled to get colorless liquid, 52.36 g (78% yield), b.p. 65-67° C./0.3 mmHg.

Alternative Procedure:

4-Toluenesulfonic acid monohydrate (51.3 g) in acetone (275 mL) was stirred with 2,2-dimethoxy propane (75 mL) and toluenesulfonic acid monohydrate (1.3 g) for 18 hr at room temperature, and worked up in a similar manner as indicated in the procedure above, 52.12 g (76% yield), b.p. 72-75° C./0.65 mmHg. Mass spec: m/z 161 (M++1). Anal Calcd for $C_8H_{15}O_3$: C, 59.98; H, 10.07%. Found: C, 59.62; H, 10.07%. $^1$H NMR (CDCl$_3$) δ ppm: 0.83 (s, 3H), 1.40 (s, 3H), 1.44 (s, 3H), 3.59-3.69 (m, 6H). $^{13}$C NMR: 17.69, 20.25, 27.41, 34.86, 65.90, 66.43, 98.1 (7 sp$^3$C).

EXAMPLE 6

2,2,5-Trimethyl-5-[(3-bromophenoxy)]methyl-1,3-dioxane via Ulmann Ether Reaction A mixture of 3-bromoiodobenzene (0.85 g, 3.0 mmol), 2,2,5-trimethyl-5-hydroxymethyl-1,3-dioxane (1.25 g, 7.8 mmol), copper (I) iodide (0.065 g, 0.38 mmol), 1,10-phenanthroline (0.122 g, 0.68 mmol), and cesium carbonate (2.54 g, 7.8 mmol) was heated to 110° C. in an oil bath and held at this temperature for 20 hr. After cooling, the mixture was diluted with toluene, filtered, and the filtrate was transferred to a column of silica gel. Elution with toluene gave the product as a colorless liquid, 0.56 g (59% yield). The product solidifies on standing with hexanes, m.p. 66-67° C. Mass spec: m/z 314, 316 (M$^+$). Anal Calcd for $C_{14}H_{19}BrO_3$: C, 53.34; H, 6.08; Br, 25.35%. Found: C, 52.98; H, 5.91; Br, 25.44%. $^1$H NMR (CDCl$_3$) δ ppm: 0.94 (s, 3H), 1.41 (s, 3H), 1.47 (s, 3H), 3.73 (dd, J=12 Hz, 2H), 4.00 (s, 2H), 6.85-6.88 (m, 1H), 7.06-7.08 (m, 1H), 7.10-7.15 (m, 2H).

EXAMPLE 7

2,2,5-Trimethyl-5-[(3-bromophenoxy)]methyl-1,3-dioxane via Mitsunobu Reaction

To a mechanically stirred mixture of 3-bromophenol (26.14 g, 0.1511 mol), 2,2,5-trimethyl-5-hydroxymethyl-1,3-dioxane (31.98 g, 0.20 mol), triphenylphosphine (59.32 g, 0.226 mol), and THF (250 mL), cooled to −2° C., a solution of diisopropyl azodicarboxylate (DIAD), 4.6 mL, 0.2265 mol) in THF (50 mL) was added dropwise over 45 min, and the mixture was allowed to warm up to room temperature. After 3 days, THF was removed, and the residue was stirred in a mixture of toluene and heptane (1:1, 300 mL), and filtered. The solids were washed with the same mixture of solvents (200 mL), and the combined filtrates were washed with dilute sodium hydroxide solution, water, and saturated sodium chloride solution, dried, and concentrated. The residue was chromatographed over silica gel. Elution with toluene-heptane (1:1) removed some unreacted triphenylphosphine. The product came in toluene-heptane (3:1) eluates and, on standing with pentane, solidified, 40.69 g (85% yield), m.p. 67-70° C. Mass spec: m/z 314, 316 (M$^+$). Anal Calcd for $C_{14}H_{19}BrO_3$: C, 53.34; H, 6.08; Br, 25.35%. Found: C, 53.37; H, 5.97; Br, 25.35%.

EXAMPLE 8

3-[5-(2,2,5-Trimethyl-1,3-dioxanyl)methoxy]-diphenylamine

A mixture of 2,2,5-trimethyl-5-(3-bromophenoxy)-methyl-1,3-dioxane (7.88 g, 25.0 mmol), aniline (4.6 mL, 50.0 mmol), and toluene (100 mL) was azeotroped dry under nitrogen and cooled. Bis(dibenzylideneacetone)palladium(O) (0.172 g, 0.3 mmol), 1,1'-bis (diphenylphosphino)ferrocene (0.21 g, 0.38 mmol), and sodium t-butoxide (3.64 g, 37.9 mmol) were added, and the mixture was held at 88° C. for 4 hr. After cooling, the mixture was treated with water, the organic phase was dried and transferred to a column of silica gel. Elution with toluene gave the product, which, on standing in hexanes, solidified, 7.2 g (88% yield), m.p. 93-96° C. Recrystallization from heptane raised the m.p. to 104-105° C. in 97% recovery. Mass spec: m/z 327 (M$^+$). Anal Calcd for $C_{20}H_{25}O_3$: C, 73.37; H, 7.70; N, 4.28%. Found: C, 73.21; H, 7.62; N, 4.13%. $^1$H NMR (CDCl$_3$) δ ppm: 0.95 (s, 3H), 1.40 (s, 3H), 1.46 (s, 3H), 3.66 (d, J=12 Hz, 2H), 3.80 (d, J=12.1 Hz, 2H), 3.96 (s, 2H), 6.69 (broad s, 1H), 6.49-6.52 (m, 1H), 6.63-6.66 (m 2H), 6.92-6.96 (m, 1H), 7.07-7.7.10 (m, 2H), 7.15 (t, J=8.08 Hz, 1H), 7.25-7.29 (m, 2H). $^{13}$C NMR: 18.16, 20.38, 27.36, 34.30, 66.50, 70.50 (6 sp$^3$ C), 98.14, 104.18, 107.04, 110.37, 118.36, 121.29, 129.49, 130.16, 143.04, 144.59, 160.54 (11 sp$^2$ C).

EXAMPLE 9

2,4,6-Tris(7-bromo-9,9-diethylfluoren-2-yl)-1,3,5-triazine

To trifluoromethanesulfonic acid (11.0 ml), cooled in a bath of ice and salt, 7-bromo-9,9-diethylfluorene-2-carbonitrile (Example 4; 10.17 g) was added in portions and then allowed to warm up to room temperature. After 24 hr, the thick reaction mixture was diluted with chloroform (10 mL) and stirred for an additional 24 hr. Then the mixture was poured into crushed ice, and the slurry was treated with ammonium hydroxide until the mixture was colorless. Chloroform was allowed to evaporate, and the mixture was filtered to get the crude triazine, 10.62 g. This was recrystallised from a mixture of toluene and heptanes with clarification, and the product was dried at 150° C., 9.68 g (95% Yield), m.p. 175-177° C. Mass spec: m/z 975, 977, 979, 981 (M$^+$). Anal Calcd for $C_{54}H_{48}N_3Br_3$: C, 66.27; H, 4.94; N, 4.29; Br, 24.49%. Found: C, 66.65; H, 5.04; N, 4.27; Br, 24.63%. $^1$H NMR (CDCl$_3$) δ ppm: 0.43 (t, J=7.32 Hz, 18H), 2.13 (sextet, J=6.95 Hz, 6H), 2.26 (sextet, J=7.13 Hz, 6H), 7.53-7.56 (m, 6H), 7.70 (d, J=7.92 Hz, 3H), 7.91 (d, J=7.92 Hz, 3H), 8.74 (d, J=1.04 Hz, 3H), 8.86 (dd, J=1.46 and 7.98 Hz, 3H). $^{13}$C NMR: 8.75, 32.85, 56.84 (3 sp$^3$ C), 120.05, 122.01, 122.45, 123.42, 126.63, 128.75, 130.45, 135.69, 139.86, 145.09, 150.12, 153.45, and 171.83 (13 sp$^2$ C).

EXAMPLE 10

2,4,6-Tris{7-(3-[5-(2,2,5,-trimethyl-1,3-dioxanyl) methoxy]diphenylamino)-9,9-diethylfluoren-2-yl}-1,3,5-triazine A mixture of 2,4,6-tris(7-bromo-9,9-diethylfluoren-2-yl)-1,3,5-triazine (10.3 g, 10.5 mmol), 3-[5-(2,2,5-trimethyl-1,3-dioxanyl)methoxy]-diphenylamine (10.83 g, 33.1 mmol), and toluene (225 mL) was azeotroped dry under nitrogen, and cooled. Bis(dibenzylideneacetone)palladium(O) (0.28 g, 0.49 mmol), 1,1'-bis(diphenylphosphino)ferrocene (0.278 g, 0.5 mmol), and sodium t-butoxide (4.52 g, 47.0 mmol) were then added, and the mixture was held at 75° C. for 20 hr. After cooling, the mixture was diluted with toluene and water, and the organic phase was washed with water, dried, and concentrated. The column was first eluted with toluene to remove the diphenylamine starting material and then with 2% ethyl acetate-toluene to get the product, 16.58 g (92% yield). The solvent free product had m.p. 143-146° C. MALDI (terthiophene as matrix) Mass spec: m/z 1717.7, 1718.7, 1719.7, 1720.7, 1721.8, 1722.8. Anal Calcd for $C_{114}H_{120}N_6O_9$: C, 79.69; H, 7.04; N, 4.89. Found: C, 79.81; H, 7.04; N, 4.80%. $^1$H NMR (CDCl$_3$) δ ppm: 0.46 (t, J=7.3 Hz, 18H), 0.92 (s, 9H), 1.38 (s, 9H), 1.44 (s, 9H), 2.02 (sextet, J=7.03, 6H), 2.19 (sextet, J=6.95 Hz, 6H), 3.63 (d, J=12 Hz, 6H), 3.77 (d, J=11.96 Hz, 6H), 3.92 (s, 6H), 6.63 (dd, J=1.84, and 8.16 Hz, 3H), 6.70-6.75 (m, 6H), 7.04-7.31 (m, 24H), 7.69 (d, J=8.20 Hz, 3H), 7.84 (d, J=8.0 Hz, 3H), 8.72 (s, 3H), 8.84 (dd, J=1.40, and 8.00 Hz, 3H). $^{13}$C NMR: 8.86, 18.13, 20.26, 27.42, 32.80, 34.25, 56.42, 66.44, 70.42 (9 sp$^3$C), 98.12, 108.94, 110.56, 116.74, 119.19, 119.23, 121.37, 123.06, 123.19, 123.58, 124.56, 128.67, 129.39, 129.93, 134.57, 135.79, 145.99, 147.90, 148.23, 149.16, 150.34, 152.66, 160.29, 171.80 (24 sp$^2$C).

EXAMPLE 11

2,4,6-Tris{7-(3-(2,2,-di(hydroxymethyl)-propyloxy)] diphenylamino]-9,9-diethylfluoren-2-yl}-1,3,5-triazine (AF-452-6OH)

Dowex resin (Dowex-50WX2-100, 50 g) was suspended in methanol, filtered, and washed with methanol. To a solution of 2,4,6-tris{7-(3-[5-(2,2,5,-trimethyl-1,3-dioxanyl)methoxy]diphenylamino)-9,9-diethylfluoren-2-yl}-1,3,5-triazine (Example 10) (10 g) in a mixture of THF (200 mL) and methanol (200 mL), the washed Dowex resin was added, and the mixture was stirred at 40° C. for 22 hr. After cooling to room temperature, 28% ammonium hydroxide (20 mL) was added, and the mixture was filtered. The resin was washed with THF containing ammonium hydroxide, and the filtrate was concentrated. The residue was suspended in toluene (100 mL), and the suspension concentrated. The residue was transferred to a column of silica gel. The column was first eluted with ethyl acetate and then with 10% THF-ethyl acetate. The residue remained on concentration of the latter fractions was dissolved in THF (100 mL) and water (50 mL), and treated with lithium hydroxide monohydrate (2.13 g). After 6 hr at 45° C., the ethylacetate free product solution was treated with ammonium chloride (2.7 g) to discharge the orange color and then concentrated. The product suspension in water was collected, redissolved in THF (100 mL) and water (40 mL), and filtered. THF was removed using a stream of nitrogen and the lost volume was periodically made up with water. The suspension of the product was filtered, and dried, 8.34 g (90%), m.p. 186-189° C. MALDI Mass spec: m/z 1597.0, 1598.0, 1599.0, 1600.1 (M$^+$). Anal Calcd for $C_{105}H_{108}N_6O_9$: C, 78.92; H, 6.81; N, 5.26%. Found: C, 78.74; H, 6.90; N, 5.15%. $^1$H NMR (CDCl$_3$) δ ppm: 0.46 (t, 18H), 0.92 (s, 9H), 2.02 (m, 6H), 2.15 (m, 6H), 2.18 (m, 6H), 3.65 (m, 6H), 3.74 (m, 6H), 3.88 (s, 6H), 6.68 (d, 3H), 6.83 (m, 6H), 7.04 (m, 6H), 7.16 (m, 12H), 7.36 (m, 6H), 7.69 (d, 3H), 7.86 (d, 3H), 8.51 (s, 3H), 8.85 (d, 3H). $^{13}$C NMR: 8.71, 17.08, 32.64, 40.71, 56.27, 67.90, 71.40 (7 sp$^3$C), 108.75, 110.03, 116.80, 119.10, 121.26, 123.08, 123.52, 124.50, 128.56, 129.29, 129.90, 134.49, 135.78, 145.77, 147.67, 147.99, 149.16, 150.18, 152.55, 159.73, and 171.66 (21 sp$^2$C).

EXAMPLE 12

2,2',2''-(3,3',3''-(7,7',7''-(1,3,5-triazine-2,4,6-triyl)tris(9,9-diethyi-9H-fluorene-7,2-diyl))tris(phenylazanediyl)tris(benzene-3,1-diyl))tris(oxy)tris(methylene)tris(2-methylpropane-3,2,1-triyl)hexaacetate (AF-452-GOH-Hexaacetate)

To a cooled solution of 2,4,6-tris{7-[3-(2,2-di(hydroxymethyl)-propyloxy)]diphenylamino]-9,9-diethylfluoren-2-yl)}-1,3,5-triazine (AF-452-60H, 0.418 g) in pyridine (3 mL), acetic anhydride (2 mL) was added, and the mixture was poured into water. The separated solids were transferred to a column of silica gel, and the column was eluted with 20% ethyl acetate/toluene to get the hexa acetate (0.358 g). A mass spectrum was not obtained due to decomposition of the compound under electron impact conditions. Anal Calcd for $C_{117}H_{120}N_6O_{15}$: C, 75.95; H, 6.54; N, 4.54%. Found: C, 75.72; H, 6.64; N, 4.29%. $^1$H NMR (CDCl$_3$) δ ppm: 0.46 (t, 18H), 1.06 (s, 9H), 2.02 (s, 18H), 2.00-2.03 (m, 6H), 2.04-2.20 (m, 6H), 3.76 (s, 6H), 4.08 (s, 12H), 6.56-6.58 (dd, 3H), 6.68-6.74 (m, 6H), 7.01-7.09 (m, 6H), 7.15-7.19 (m, 12H), 7.26-7.32 (m, 6H), 7.70 (d, 3H), 7.84 (d, 3H), 8.72 (s, 3H), and 8.84 (dd, 3H).

EXAMPLE 13

2,2',2''-(3,3',3''-(7,7',7''-(1,3,5-triazine-2,4,6-triyl)tris(9,9-diethyi-9H-fluorene-7,2-diyl))tris(phenylazanediyl)tris(benzene-3,1-diyl))tris(oxy)tris(methylene)tris(2-methylpropane-3,2,1-triyl) hexakis(2-ethylacrylate) (AF-452-GOH-hexamethacrylate)

To a solution of 2,4,6-tris{7-[3-(2,2-di(hydroxymethyl)-propyloxy)]diphenylamino]-9,9-diethylfluoren-2-yl)}-1,3, 5-triazine (AF-452-60H, 1.6 g) in a mixture of triethylamine (2 mL), and THF (20 mL), cooled in an ice bath, methacryloyl chloride (1.4 mL) was syringed in, and stirred for 18 hr. After filtration, the filtrate was concentrated, extracted into toluene, and the extract was washed with water, dried, and concentrated. The residue was chromatographed over silica gel. Elution with 20% ethyl acetate/toluene gave the product, 0.26 g (13%). Anal Calcd for $C_{129}H_{132}N_6O_{15}$: C, 77.22; H, 6.63; N, 4.19%. Found: C, 77.02; H, 6.76; N, 4.19%. Proton NMR was too complex to be interpreted. Oligomerization of the initially formed methacrylated products during work up is suspected.

Having thus described exemplary embodiments of the present invention, it should be noted by those skilled in the art that the disclosures herein are exemplary only and that alternatives, adaptations and modifications may be made within the scope of the present invention.

We claim:

1. A two-photon active tris(diarylamino-9,9-dialkylfluorenyl)-1,3,5-triazine compound having the structure:

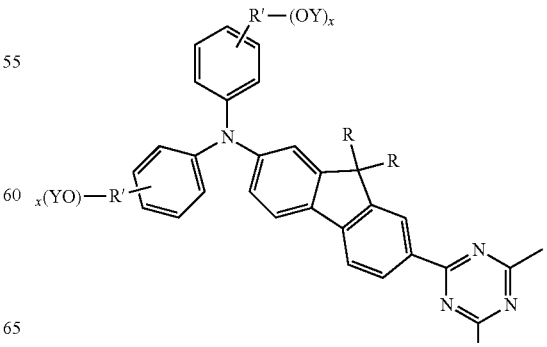

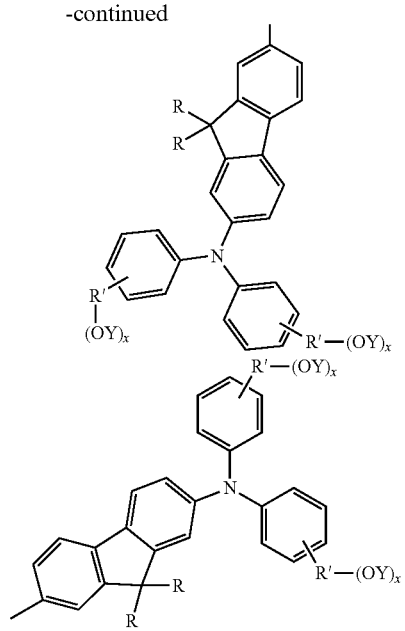

wherein Y is hydrogen, a thermally self-polymerizable acrylic, or a methacrylic group;

R is an alkyl group of the formula —$C_mH_{2m+1}$ where m is from 1 to 6 or an alkylether group of the formula —$(CH_2CH_2O)_p$Me where p is from 1 to 5;

R' is an alkyl group; and the R'—$(OY)_x$ groups are attached to the phenyl rings of the triarylamine moiety either in a para position or a meta position and x ranges from 1 to 3.

2. The two photon active tris(diarylamino-9,9-dialkylfluorenyl)-1,3,5-triazine compound of claim 1, wherein the alkyl group of the R' has the formula —$C_mH_{2m}$ where m is from 1 to about 6.

* * * * *